(12) United States Patent
Finnegan

(10) Patent No.: US 10,131,925 B2
(45) Date of Patent: Nov. 20, 2018

(54) METHOD FOR PRODUCING ESTERS OF 3-HYDROXYPROPIONIC ACID

(71) Applicant: Verdant Bioproducts Limited, Corby, Northhamptonshire (GB)

(72) Inventor: Irene Finnegan, Corby (GB)

(73) Assignee: VERDANT BIOPRODUCTS LIMITED, Milton Keynes (GB)

( * ) Notice: Subject to any disclaimer, the term of this patent is extended or adjusted under 35 U.S.C. 154(b) by 0 days.

(21) Appl. No.: 15/116,739

(22) PCT Filed: Feb. 6, 2015

(86) PCT No.: PCT/GB2015/050329
§ 371 (c)(1),
(2) Date: Aug. 4, 2016

(87) PCT Pub. No.: WO2015/118341
PCT Pub. Date: Aug. 13, 2015

(65) Prior Publication Data
US 2016/0348137 A1 Dec. 1, 2016

(30) Foreign Application Priority Data

Feb. 7, 2014 (GB) .................................. 1402173.7

(51) Int. Cl.
*C12N 9/96* (2006.01)
*C12P 7/62* (2006.01)
(52) U.S. Cl.
CPC ..................................... *C12P 7/62* (2013.01)
(58) Field of Classification Search
None
See application file for complete search history.

(56) References Cited

U.S. PATENT DOCUMENTS

| 7,186,541 B2 * | 3/2007 | Gokarn ............... C12N 9/0004 435/232 |
| 2010/0021978 A1 | 1/2010 | Burk et al. |
| 2016/0348017 A1 | 12/2016 | Finnegan |
| 2017/0233773 A1 | 8/2017 | Finnegan |

FOREIGN PATENT DOCUMENTS

| JP | 2012213346 A | 11/2012 |
| WO | 0242418 A2 | 5/2002 |
| WO | 2013011292 A2 | 1/2013 |

OTHER PUBLICATIONS

Coban, E.P. et al, "Effect of various carbon and nitrogen sources on cellulose synthesis by Acetobacter lovaniensis HBB5", African Journal of Biotechnology, vol. 10 (27), Jun. 15, 2011; pp. 5346-5354.
Coban, E.P. et al, "Evaluation of different pH and temperatures for bacterial cellulose production in HS (Hestrin-Scharmm) medium and beet molasses medium", African Journal of Microbiology Research, vol. 5 (9), May 4, 2011, pp. 1037-1045.
Hall, A.N. et al, "Nutritional Requirements of Acetobacter Species: Inorganic Ammonium Salts as Sources of Nitrogen", Journal of Applied Bacteriology, vol. 19 No. 1, 1956; pp. 31-35.
International Search Report for International Application PCT/GB2015/050329; International Filing Date: Feb. 6, 2015; dated Apr. 9, 2015; 7 pages.
UK Search Report for GB Application No. 1402173.7; Filing Date: Feb. 6, 2014; dated Jan. 26, 2015; 3 pages.
Written Opinion of the International Searching Authority for International Application PCT/GB2015/050329; International Filing Date Feb. 6, 2015; dated Apr. 9, 2015; 11 pages.

* cited by examiner

*Primary Examiner* — Hope Robinson
(74) *Attorney, Agent, or Firm* — Cantor Colburn LLP

(57) ABSTRACT

There is described a method for producing an ester of 3-hydroxypropionic acid, the method comprising: culturing an *Acetobacter lovaniensis* bacterium in a growth medium containing phosphate at a level which is more than 1 g/liter, wherein culturing of the bacterium produces the ester of 3-hydroxypropionic acid.

19 Claims, 1 Drawing Sheet

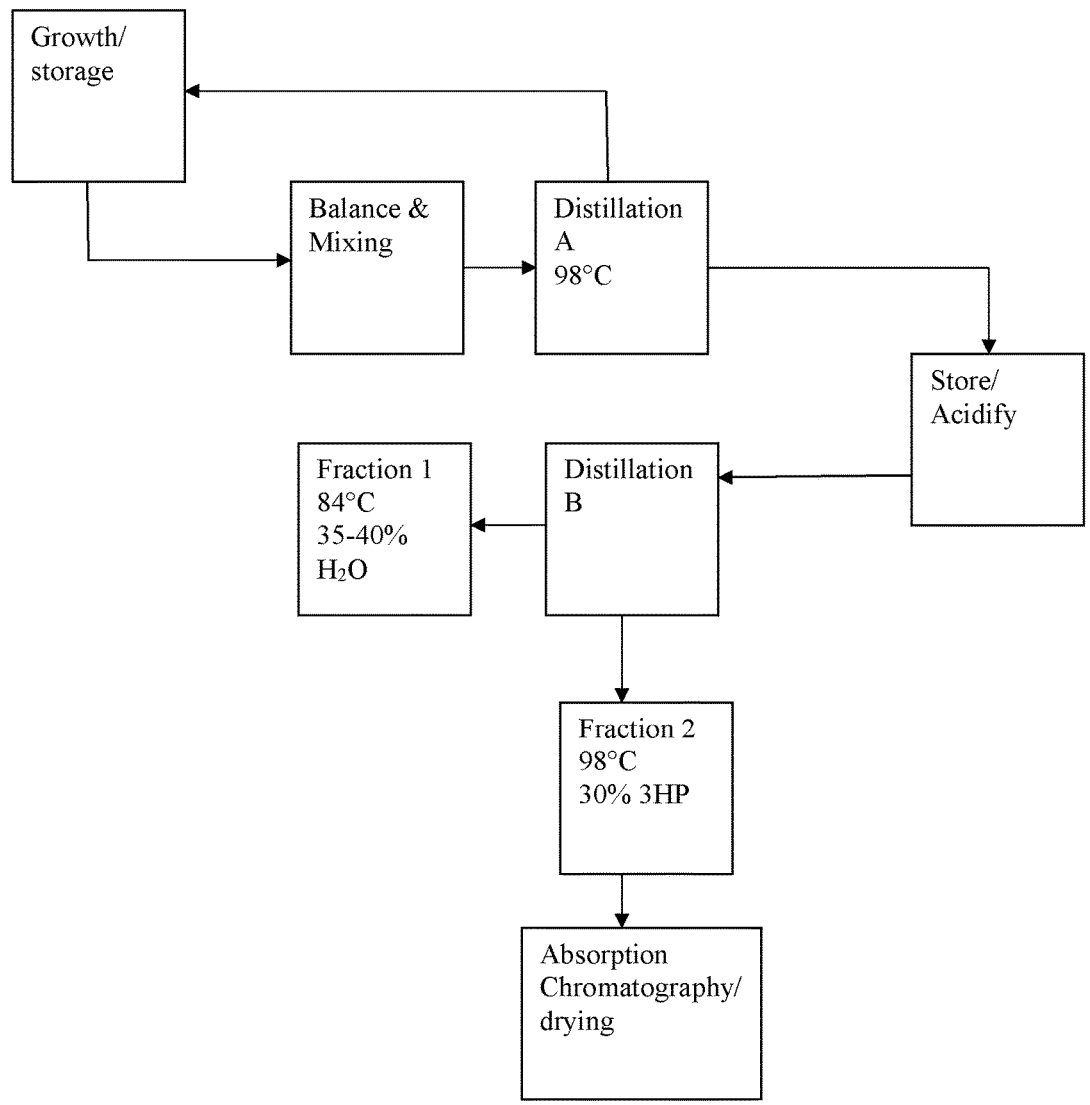

METHOD FOR PRODUCING ESTERS OF 3-HYDROXYPROPIONIC ACID

CROSS-REFERENCE TO RELATED APPLICATIONS

This application is a National Stage application of International Application No. PCT/GB2015/050329, filed Feb. 6, 2015, which claims the benefit of GB Application No. 1402173.7, filed Feb. 7, 2014, both of which are incorporated by reference in their entirety herein.

FIELD OF THE INVENTION

The present invention relates to a method for producing esters of 3-hydroxypropionic acid by culturing an *Acetobacter* microorganism under particular growth conditions. These esters can be hydrolysed to form 3-hydroxypropionic acid (3HP).

BACKGROUND TO THE INVENTION

Many microorganisms have been shown to produce hydroxycarboxylic acids such as 3-hydroxypropionic acid (Andreeken, B., and Steinbuchel, A., Applied and Environmental Microbiology (2010), 76, 4919-4925), 3-hydroxybutyric acid (Aslim, B., Caliskan, F., Beyatli, Y. and Gunduz, U., FEMS Microbiol. Lett (1998), 159, 293-297), 3-hydroxyvaleric acid (Steinbuchel, A., Debzi, E-M., Marchessault, R. H and Timm, A., Applied Microbiology and Biotechnology (1993), 39, 443-449) and their polymers in the form of polyalkanoates (US20120129232). Generally, hydroxycarboxylic acids and their corresponding polyalkanoates are produced in response to nutrient limited growth conditions (Brigham, C. J., Kurosawa, K., Rha, C., and Sinskey, A. J., S3 Microbial and Biochemical Technology (2011)). Production of hydroxycarboxylic acids, in particular, 3-hydroxypropionic acid, is of commercial importance as it is easily converted to acrylic acid and other chemicals. As a result, 3-hydroxypropionic acid (CAS number 503-66-2) is a valuable platform chemical.

The production of 3-hydroxypropionic acid by genetically modified microorganisms has been the focus of a number of patents (US20090325248, US20100021978, WO2012/0301935, US2012244588 and US20110125118). These patents describe fermentative processes whereby sources of carbohydrate such as sugars or glycerol are converted to 3HP through known modified pathways. Yields are described in various formats, WO2012/0301935 gives results of 0.97 g of 3HP per gram of added glycerol and US20110125118 describes yields in terms of 0.05 g/g dry cell weight/hour or 0.05 g/liter/hour.

More recently, the conversion of carbon dioxide to 3-hydroxypropionic acid was described in *Pyrococcus furiosus* (WO2013/067326). This organism has been engineered to use carbon dioxide and hydrogen gas to produce 3HP either by cell free extracts or whole cells of the recombinant strain. However, this organism is genetically modified and requires a growth temperature of 70 to 73° C.

Harvested 3HP is converted to acrylic acid via well-established chemical procedures. 5 However, the major issue with all biological processes is that while the yields of 3HP are at commercially useful levels, the molecule is difficult and costly to extract from the background of other material present in the spent bacterial media. In addition, the cost of starter feed stocks also prohibits the commercialisation of biological 3HP production.

WO2013/011292 describes a microorganism which is capable of producing long chain aliphatic carboxylic acids. This document describes a particular strain referred to as *Acetobacter lovaniensis* FJ1 having accession number NCIMB 41808 (deposited at NCIMB Ltd. (Ferguson Building, Craibstone Estate, Bucksburn, Aberdeen, AB21 9YA) on 12 January 2011 under the provisions of the Budapest Treaty).

SUMMARY OF THE INVENTION

It has been surprisingly found that the *Acetobacter lovaniensis* strain described in WO2013/011292 can produce esters of 3-hydroxypropionic acid. It was not previously known that this microorganism could produce such products.

The present invention relates to a method for producing esters of 3-hydroxypropionic acid using the microorganism described in WO2013/011292. The disclosure of WO2013/011292 is incorporated herein in its entirety. This microorganism has been shown to have the ability to produce hydroxycarboxylic esters and acids on a phosphate enriched growth regime.

In a first aspect, the present invention provides a method for producing an ester of 3-hydroxypropionic acid, the method comprising: culturing an *Acetobacter lovaniensis* bacterium in a growth medium containing phosphate at a level which is more than 1 g/liter, wherein culturing of the bacterium produces the ester of 3-hydroxypropionic acid.

Preferably, the ester of 3-hydroxypropionic acid is ethyl 3-hydroxypropionate. As a result, the method is for producing ethyl 3-hydroxypropionate, the method comprising: culturing an *Acetobacter lovaniensis* bacterium in a growth medium containing more than 1 g/liter of phosphate, wherein culturing of the bacterium produces ethyl 3-hydroxypropionate.

The *Acetobacter lovaniensis* bacterium in cultured in a growth medium containing more than 1 g/liter of phosphate. 1 g/liter is the amount of phosphate ion ($PO_4^{3-}$) in the growth medium rather than the amount of the phosphate containing compound in the growth medium. For example, potassium dihydrogen phosphate ($KH_2PO_4$) has a relative molecular mass of 136. The phosphate part of this has a relative molecular mass of 95. Therefore, if 136 grams of $KH_2PO_4$ was added to 100 liters of water, there would be 1.36 g/liter of $KH_2PO_4$ in the water but there would be 0.95 g/liter of phosphate in the water.

In some embodiments, the growth medium preferably contains phosphate at a level which is more than 2 g/liter. In other embodiments, the growth medium contains phosphate at more than 3 g/liter. In further embodiments, the growth medium contains phosphate at more than 4g/liter. In particular embodiments, the growth medium contains phosphate at more than 5 g/liter. In some embodiments, the growth medium contains phosphate at more than 6 g/liter. In other embodiments, the growth medium contains phosphate at more than 7 g/liter. In further embodiments, the growth medium contains phosphate at more than 8 g/liter. In particular embodiments, the growth medium contains phosphate at more than 9 g/liter. In some embodiments, the growth medium contains phosphate at more than 10 g/liter. In other embodiments, the growth medium contains phosphate at more than 11 g/liter. In further embodiments, the growth medium contains phosphate at more than 12 g/liter. In a preferred embodiment, the growth medium contains phosphate at more than 13 g/liter. In another preferred embodiment, the growth medium contains phosphate at more than 14 g/liter.

In some embodiments, the growth medium contains phosphate at a level which is less than 150 g/liter. In other embodiments, the growth medium contains phosphate at less than 100 g/liter. In further embodiments, the growth medium contains phosphate at less than 80 g/liter. In various embodiments, the growth medium contains phosphate at less than 70 g/liter. In particular embodiments, the growth medium contains phosphate at less than 60 g/liter. In some embodiments, the growth medium contains phosphate at less than 50 g/liter. In other embodiments, the growth medium contains phosphate at less than 45 g/liter. In further embodiments, the growth medium contains phosphate at less than 40 g/liter. In particular embodiments, the growth medium contains phosphate at less than 35 g/liter. In some embodiments, the growth medium contains phosphate at less than 30 g/liter. In other embodiments, the growth medium contains phosphate at less than 25 g/liter. In further embodiments, the growth medium contains phosphate at less than 20 g/liter. In particular embodiments, the growth medium contains phosphate at less than 15 g/liter.

In some embodiments, the growth medium contains phosphate at a level which is between 1 and 150 g/liter. In other embodiments, the growth medium contains phosphate at between 2 and 100 g/liter. In further embodiments, the growth medium contains phosphate at between 3 and 80 g/liter. In various embodiments, the growth medium contains phosphate at between 4 and 70 g/liter. In particular embodiments, the growth medium contains phosphate at between 5 and 60 g/liter. In some embodiments, the growth medium contains phosphate at between 6 and 50 g/liter. In other embodiments, the growth medium contains phosphate at between 7 and 45 g/liter. In further embodiments, the growth medium contains phosphate at between 8 and 40 g/liter. In particular embodiments, the growth medium contains phosphate at between 9 and 35 g/liter. In some embodiments, the growth medium contains phosphate at between 10 and 30 g/liter. In other embodiments, the growth medium contains phosphate at between 11 and 25 g/liter. In further embodiments, the growth medium contains phosphate at between 12 and 20 g/liter. In particular embodiments, the growth medium contains phosphate at between 13 and 15 g/liter.

The growth medium can be any suitable growth medium which allows the *Acetobacter lovaniensis* bacterium to grow and reproduce, and to produce the ester of 3-hydroxypropionic acid. The growth medium may contain various ingredients/nutrients to allow the bacterium to grow and reproduce. The growth medium may contain one or more of the following additives: a potassium salt, a magnesium salt, a manganese salt, an iron salt, a copper salt, a cobalt salt, a sodium salt, a zinc salt, a calcium salt, a molybdenum salt, a chloride, a sulphate, a molybdate and a carbonate. These additives are generally present in the growth medium at between 0.01 and 2 g/liter.

In some embodiments, the growth medium may have one or more of the following additives in the amount specified:

| Ingredient | g/1000 ml |
| --- | --- |
| Potassium Hydrogen Phosphate | 10-30 |
| Magnesium Chloride | 0.1-2 |
| Manganese Chloride | 0.01-0.1 |
| Ferric Chloride | 0.01-0.1 |

-continued

| Ingredient | g/1000 ml |
| --- | --- |
| Copper Sulphate | 0.01-0.1 |
| Cobalt Chloride | 0.01-0.1 |
| Sodium molybdate | 0.01-0.1 |
| Zinc Chloride | 0.1-1 |

In a particular embodiment, the growth medium has the following composition:

| Ingredient | g/1000 ml |
| --- | --- |
| Potassium Hydrogen Phosphate | 20 |
| Magnesium Chloride | 1 |
| Manganese Chloride | 0.05 |
| Ferric Chloride | 0.05 |
| Copper Sulphate | 0.05 |
| Cobalt Chloride | 0.05 |
| Sodium molybdate | 0.05 |
| Zinc Chloride | 0.5 |

Preferably, the growth medium does not contain an exogenous source of nitrogen. This is not required as the bacterium can fix nitrogen which is dissolved in the growth medium from the atmosphere.

The bacterium can fix carbon dioxide. Therefore, the growth medium does not require an exogenous source of carbon other than carbon dioxide dissolved in the growth medium from the atmosphere. However, in some embodiments, before the bacterium is cultured or during culturing, carbon dioxide can be bubbled through the growth medium to increase the amount of carbon dioxide dissolved in the growth medium. The bacterium can use carbon dioxide as the sole source of carbon.

In some embodiments, glycerol is added to the growth medium as an additional source of carbon. Preferably, this is done after the bacterium has started to grow and reproduce.

The growth medium may have a pH of between 3.5 and 9. Preferably, the growth medium has a pH of between 4 and 7. The pH of the growth medium is preferably not too low as acidic conditions can cause the ester of 3HP to hydrolyse to 3HP which can reduce the recovery yield. In a particular embodiment, the pH of the growth medium is about 4.5.

The growth medium is preferably aqueous such that the nutrients/additives are dissolved in water.

The bacterium is generally cultured at a temperature of between 0° C. and 60° C. Preferably, the bacterium is cultured at a temperature of between 10° C. and 40° C. In some embodiments, the bacterium is cultured at a temperature of between 15° C. and 30° C.

The bacterium is generally cultured until the growth culture reaches an optical density when measured at 600 nm ($OD_{600}$) of between 0.75 and 1.00.

During culturing, the culture can be diluted with additional growth medium to increase the volume of culture. Therefore, when it is desired to extract the ester of 3HP, the culture should have a final optical density of between 0.75 and 1.00.

The bacterium may be cultured for between 12 and 36 hours. In some embodiments, the bacterium may be cultured for between 18 hours and 30 hours.

The ester of 3-hydroxypropionic acid is produced by culturing an *Acetobacter lovaniensis* bacterium. The bacterium can be any suitable *Acetobacter lovaniensis* bacterium which can produce an ester of 3-hydroxypropionic acid. This includes strain FJ1 (having accession number NCIMB 41808) and similar strains which are related to or derived from FJ1. The term "derived from" means that FJ1 can be modified or mutated to produce further bacteria. For example, genes may be inserted or removed from FJ1. Bacteria which are derived from FJ1 should be functionally equivalent to FJ1 and should be able to produce an ester of 3-hydroxypropionic acid. Further, the derived bacterium should be able to grow under the same conditions as FJ1. Preferably, the bacterium is strain FJ1 having accession number NCIMB 41808. A bacterium can be identified as an *Acetobacter lovaniensis* bacterium by methods which are well known to those skilled in the art, for example, by using 16S rDNA analysis.

The bacterium produces the ester of 3-hydroxypropionic acid as it grows so once the culturing of the bacterium has been completed, the ester of 3-hydroxypropionic acid will be present in the growth medium. The ester of 3-hydroxypropionic acid can then be extracted, if desired. The method may further comprise the step of separating the ester of 3-hydroxypropionic acid from the growth medium. This can be in a first separation step. This can be done in any suitable way and a number of methods will be apparent to one skilled in the art.

For example, the ester of 3-hydroxypropionic acid can be separated using distillation, including standard distillation, fractional distillation, vacuum distillation, distillation with an entrainer, solvent extraction followed by recovery with distillation, and continuous distillation. Other separation methods include membrane perfusion, electro-chemical separation, or the use of critical carbon dioxide.

If distillation is carried out at 1 atmosphere (rather than at reduced pressure as in vacuum distillation) using, for example, a side arm condenser, the 3HP ester will be contained in the first 10-15% of the distillate and will be collected at a temperature of between 95° C. and 100° C., in particular, at about 98° C. Generally, the 3HP ester is collected as an azeotrope.

Once the ester of 3-hydroxypropionic acid has been separated, it can be converted to 3HP. This involves the breaking down of the ester linkage to produce 3HP. Suitable methods for this are well known to a skilled person. For example, conversion to 3HP can be done by acidifying the sample containing the ester of 3-hydroxypropionic acid to cause acid hydrolysis of the ester. This can be done by adding an acid to the 3HP ester. Suitable acids include hydrochloric acid and sulphuric acid. Alternatively, the 3HP ester can be hydrolysed using an alkali. This will produce a 3-hydroxypropionate salt which can be converted to the acid form, for example, using a concentrated acid.

Once converted to 3HP, a second separation step can then take place to separate the 3HP from any other products which are present after the conversion process, e.g. alcohol. This second separation can be carried out using any suitable method. For example, the 3HP can be separated using distillation, including standard distillation, fractional distillation, vacuum distillation, distillation with an entrainer, solvent extraction followed by recovery with distillation, and continuous distillation. Other separation methods include membrane perfusion, electro-chemical separation, or the use of critical carbon dioxide.

If distillation is carried out at 1 atmosphere (rather than at reduced pressure as in vacuum distillation) using, for example, a fractionating column, the 3HP will distil at a temperature of between 95° C. and 100° C., in particular, at about 98° C. Generally, the 3HP is collected as an azeotrope.

After the second separation step, a relatively pure sample of 3HP is produced, generally as an aqueous solution.

Once separated, the 3HP may be dried to remove some of the water. This can be done with agents such as, but not limited to, chloride salts (calcium or sodium) or molecular sieve 3A.

As indicated above, 3HP is a platform chemical so it can then be further processed into other chemicals such as 3-hydroxypropionate salts (including ammonium, sodium and calcium 3-hydroxypropionate), 3-hydroxypropionate esters (e.g. methyl, propyl and butyl esters), acrylic acid, acrylates (the salts, esters and conjugate bases of acrylic acid and its derivatives), polyacrylic acid, acrylate polymers, acrylonitrile, acrylamide, acrolein, 1,3 propanediol and Reuterin.

In a particular embodiment, there is provided a method for producing 3-hydroxypropionic acid, the method comprising:
culturing *Acetobacter lovaniensis* strain FJ1 having accession number NCIMB 41808 in a growth medium containing phosphate at a level which is between 10 and 30 g/liter, wherein culturing of the bacterium produces ethyl 3-hydroxypropionate;
separating the ethyl 3-hydroxypropionate from the growth medium;
converting the ethyl 3-hydroxypropionate to 3-hydroxypropionic acid; and
separating the 3-hydroxypropionic acid.

In this embodiment, the phosphate level is described as being between 10 and 30 g/liter. However, any of the levels described above can be used in this particular embodiment. For example, the phosphate level may be more than 1 g/liter or the phosphate level may be between 13 and 15 g/liter, or any of the embodiments in between.

It is thought that the enzymes responsible for producing the 3HP ester are extracellular of the bacterium. These enzymes function regardless of whether the cells of the bacterium are present. Therefore, in another aspect of the invention, there is provided a method for producing an ester of 3HP, the method comprising: providing an aqueous medium containing a cell-free extract of an *Acetobacter lovaniensis* bacterium cultured in a growth medium containing phosphate at a level which is more than 1 g/liter, wherein the 3HP ester is produced in the aqueous medium.

The steps described above for the method of the first aspect of the invention, for example, relating to separating the 3HP ester, etc. are equally applicable to this aspect of the invention.

The medium can be produced by culturing the bacterium for a period of time to allow the enzyme systems to be produced in the medium. The cell-free extract can be prepared by removing the cells of the bacterium from the medium after culturing, for example, by repeated ultra-filtration.

In a further aspect of the invention, there is provided an aqueous medium containing a cell-free extract of an *Acetobacter lovaniensis* bacterium cultured in a growth medium containing phosphate at a level which is more than 1 g/liter.

DETAILED DESCRIPTION OF THE INVENTION

The invention will now be described in detail by way of example only with reference to the figures in which:

FIG. 1 is a flow diagram showing the synthesis of 3HP esters by *Acetobacter lovaniensis* FJ1 (growing on carbon dioxide in the presence of elevated levels of phosphate) and its subsequent recovery.

Overview

In the presence of enriched levels of phosphate, and optionally in the absence of an exogenous source of nitrogen and carbon, *Acetobacter lovaniensis* FJ1 produces a different set of metabolites including, but not limited to, hydroxy-carboxylic acids. 3-hydroxypropionic acid is produced at a commercially useful level (without the need for nitrogen limitation) and this is converted to the ethyl ester in vivo.

Without wishing to be held to a particular theory, it is thought that there is a metabolic switch to carbon dioxide fixation via the hydroxyl propionate cycle (Tabita, F. J., PNAS (2009), 106, 21015-21016; Strauss, G. And Fuchs. G., Eur. J. Biochem (1993), 215, 633-643) in the presence of elevated levels of phosphate. In addition, nitrogen fixation via a nitrogenase enzyme type complex results in the generation of hydrogen (Tamagnini P., Axelssen R., Lindberg P., Oxelfelt F., Wenschiers R. and Lindblad P., Microbiology and Molecular Biology Reviews (2002), 66, 11-20) which is utilised by hydrogenase enzymes and balances the redox system of the organism. While carbon and nitrogen assimilation has been noted in other organisms (Levican G., Ugalde J. A., Ehrenfeld M., Maass A., and Parada P., BMC Genomics (2008), 581, 1186; Dubbs J. M. and Tabita F. R., Fems Microbiol Rev. (2004), 28, 353-356; McKinlay J. B. and Harwood C. S., PNAS (2010), 1073, 1-7), the use of carbon dioxide fixation as a redox recycling mechanism via a nitrogenase system has only been previously noted in anoxygenic phototrophic bacteria such as non-sulphur purple bacteria where the carbon dioxide is reduced via the Calvin Benson Basham cycle. *Acetobacter* species may be able to take advantage of this effect. While not having a functioning Calvin Benson Basham cycle, they do retain genetic elements of it, or the 3HP cycle is used to the same effect. Further to this, a proton motive force dependent efflux system for 3HP may operate as seen in *Acetobacter aceti* (Matsushita K., Inoue T., Adachi O., and Toyama H. J., Bacteriol. (2005), 187, 4346-4352).

The synthesis of esters is noted in *Acetobacter lovaniensis* FJ1. Further to this, the esterification of 3HP is believed to stem from the conversion of acetic acid to ethanol by *Acetobacter lovaniensis* FJ1 followed by esterification with 3HP. This is a new route of esterification resulting in the ethyl ester of 3HP. This product is more economical to recover from the spent bacterial media than 3HP itself. For example, recovery can be effected by simple distillation taking advantage of the azeotrope formed between the ester and water at around 98° C. This ease of recovery makes it relatively cheap to extract the 3HP ester. The ester of 3HP can then be further converted to a number of commercially useful products such as 3HP, sodium, calcium and ammonium salts of 3HP, acrylic acid, acrylates, acrylamide, acrolein and 1,3 propanediol.

Process For Producing Ethyl 3-hydroxypropionate—CAS number 623-72-3

*Acetobacter lovaniensis* FJ1 (accession number: NCIMB 41808) is grown on a minimal salt media in which sources of nitrogen are excluded and which the level of phosphate elevated. The composition of this media is shown in the table below.

TABLE 1

Composition of Minimal Salt Media Used to Grow *Acetobacter Lovaniensis* FJ1

| Ingredient | g/1000 ml |
| --- | --- |
| Potassium Hydrogen Phosphate | 20.00 |
| Magnesium Chloride | 1.00 |

TABLE 1-continued

Composition of Minimal Salt Media Used to Grow *Acetobacter Lovaniensis* FJ1

| Ingredient | g/1000 ml |
| --- | --- |
| Manganese Chloride | 0.05 |
| Ferric Chloride | 0.05 |
| Copper Sulphate | 0.05 |
| Cobalt Chloride | 0.05 |
| Sodium molybdate | 0.05 |
| Zinc Chloride | 0.50 |

The media is dissolved in water and filtered. The water used can be either distilled water or tap water. The microorganism can be grown under non-sterile conditions and further sterilisation of media and equipment either by autoclaving or some other suitable method is not required.

The microorganism is inoculated into two liter quantities of media in shake flasks or other suitable containers and grown to an A600 of between 0.75 and 1.00. Two liters of culture media is then diluted in fresh media to a volume of 10 liters and again cultured to an A600 of between 0.75 and 1.0. The volume of the culture media is increased to the desired volume by repeated splitting of the culture.

The spent bacterial media can be stored for extended periods of time of up to twelve months.

The spent bacterial media is distilled to recover products of interest using the general process shown in FIG. 1.

A standard distillation set can be used employing a flask, heater mantle, with or without fractionation column and distillation head with condenser. However, other methods of distillation such as vacuum distillation, distillation with an entrainer, solvent extraction followed by recovery with distillation and continuous distillation are also applicable. Other procedures for the recovery of metabolites such as membrane perfusion, electro-chemical separation, or recovery through the use of critical carbon dioxide can also be employed.

The ethyl 3HP can be collected as an azeotrope which forms with water at 98° C. The pooled product is then hydrolysed to the parent acid (3HP) and ethanol. The ethanol can be distilled off at around 84° C. The 3HP then again forms an azeotrope with water and distils behind this first fraction in a second fraction at 98° C. The products can be further dried with agents such as, but not limited to, chloride salts (calcium or sodium) or molecular sieve 3A.

Recoveries are measured after various pre-purification methods such as thin layer chromatography and solid phase adsorbents in tube formats. Solid phase adsorbent tubes are typically Cleanert C18 adsorbent in varying sizes of tube. The material is adsorbed onto the C18 and washed clean of contaminants and then eluted with either acetone or ethanol containing 0.1% HCl (v/v).

The concentration of 3HP ester and 3HP can be measured by high pressure liquid chromatography (HPLC). Typically 3HP is eluted isocratically using a 25 cm ODS-H, 4.6 mm column with a mobile phase of 90% ethanol: 10% water.

Individual products can be identified using mass spectroscopy with and without derivatization depending on the source and type of sample. For samples where derivatization is required, material is extracted into a suitable solvent and then treated with BSTFA (N,O-bis(trimethylsilyl)trifluoroacetamide) and TMS (trimethylsilyl). The instrument is typically run with an injection temperature of 80° C. followed by a 7° C. per minute rise to reach a full temperature of 300° C. The column is then held for 5 minutes at this temperature. A basic library search was used to identify the peaks. In a typical run, a major peak at 20.8 minutes was shown to be 3HP.

EXAMPLES

Example 1

The Growth of Organism in the Absence of Exogenously Added Nitrogen and on Carbon Dioxide as Sole Source of Carbon The organism typically has a 72 hour growth cycle when grown in the presence of elevated levels of phosphate and achieves 0.07 g/l/h dry cell weight at 20° C. Under these conditions the organism achieves the production of 0.178 g 3HP/1/h/g dry cell weight of organism.

Example 2

The Production of 3-hydroxypropionic Acid by a Simple Two Step Distillation Process The 3HP can be recovered in a simple two step distillation process.
1. Spent bacterial media is distilled in a simple distillation pot without a fractionation column but employing a side arm condenser. The 3HP ester fractions forming an azeotrope at 98° C. are collected in the first 10% of the distillate. This is "Distillation A".
2. Pooled fractions from Distillation A are re-distilled in a distillation unit employing a liter reaction flask and a packed fractionation column. Prior to distillation, the pooled fraction from Distillation A is acidified with a suitable mineral acid to hydrolyse the ester content. In Distillation B, the initial 5% containing ethanol and other volatile fractions is then removed at between 75° C. and 80° C. (Fraction 1). A second fraction (Fraction 2) of 20% by volume, enriched in 3HP is then distilled at 98° C. Fraction 2 typically contains 30% of 3HP with a purity of not less than 88%. This material corresponds with the concentration of commercially available 3HP. This product may then be further processed as shown in the following examples.

Example 3

The Synthesis of the Alkaline Earth Salts of 3HP

The aqueous 3HP solution obtained in Example 2 can further be converted to either the sodium or calcium salt by neutralization with sodium hydroxide or calcium hydroxide respectively. The soluble sodium salt can be recovered by evaporation or freeze drying. The insoluble calcium salt can be recovered by simple filtration.

Example 4

The Synthesis of the Ammonium Salt of 3HP

The ammonium salt of 3HP can be prepared by salt splitting processes such as those described in US20100099910.

Example 5

The Conversion of 3HP to Acrylic Acid

3HP can be converted to acrylic acid by conversion to the ammonium salt followed by treatment with a solid oxide dehydration catalyst (e.g. see U.S. Pat. No. 8,338,145) or other methods such as reactive distillation (e.g. see U.S. Pat. No. 8,198,481).

Example 6

The Utilisation of Alternate Substrates Conversion of Glycerol to Ethyl 3-hydroxypropionate Glycerol, including glycerol waste from biodiesel manufacture can be converted to 3-hydroxypropionic acid or acrylic acid utilising the bacterial culture as exogenous catalyst. The bacterium is grown to a cell density of 0.75 when measured at A600 and then added into a solution of 10% glycerol, which can be purified glycerol in water or biodiesel waste diluted in water to an effective concentration of 10% glycerol. The biodiesel waste does not require pre-treatment. The conversion of glycerol to 3HP can be monitored using UV visible spectroscopy, IR spectroscopy and final products analysed with HPLC and GC mass spectroscopy.

Example 7

The Conversion of 3HP to Reuterin

Reuterin is an anti-microbial agent (3-hydroxypropionaldehyde, its dimer and hydrate) inhibitory to several types of bacteria. This compound is generally produced by *L. reuteri* growing on glycerol. The 3-hydroxypropionic ethyl ester or 3-hydroxypropionic acid produced by *Acetobacter lovaniensis* FJ1 can further be converted to this compound by treatment with a suitable catalyst or by the action of a suitable enzyme such as an alcohol dehydrogenase used under appropriate conditions.

Example 8

The Enzymatic Conversion of 3HP to Acrylic Acid and Acrylic Acid Esters

The 3-hydroxypropionic acid produced in the above process can be converted to acrylic acid by use of a dehydratase enzyme under suitable conditions as used by those skilled in the art. The ester products of 3-hydroxypropionic acid such as methyl, propyl and butyl can be synthesised by the addition of molar ratios of the acid and the respective alcohol in slight excess, followed by treatment with a lipase enzyme under suitable conditions as used by those skilled in the art. The ethyl ester can be recovered from spent bacterial media by any suitable distillation method.

The invention claimed is:
1. A method for producing an ester of 3-hydroxypropionic acid, the method comprising:
culturing an *Acetobacter lovaniensis* bacterium in a growth medium containing phosphate at a level which is more than 2 g/liter and up to 30 g/liter wherein culturing of the bacterium produces an ester of 3-hydroxypropionic acid, and wherein the ester of 3-hydroxypropionic acid is ethyl 3-hydroxypropionate.
2. The method of claim 1, wherein the growth medium contains phosphate at more than 10 g/liter.
3. The method of claim 1, wherein the growth medium contains phosphate at more than 13 g/liter.
4. The method of claim 1, wherein the growth medium contains phosphate at between 10 and 30 g/liter.

5. The method of claim 1, wherein the growth medium does not contain an exogenous source of nitrogen.

6. The method of claim 1, wherein the growth medium does not contain an exogenous source of carbon.

7. The method of claim 1, wherein the growth medium contains glycerol.

8. The method of claim 1, wherein the growth medium has a pH of between 4 and 7.

9. The method of claim 1, wherein the bacterium is cultured at a temperature of between 15° C. and 30° C.

10. The method of claim 1, wherein the bacterium is cultured until the growth medium reaches an $OD_{600}$ of between 0.75 and 1.00.

11. The method of claim 1, wherein the bacterium is strain FJ1 having accession number NCIMB 41808.

12. The method of claim 1, wherein the method further comprises a step of separating the ester of 3-hydroxypropionic acid from the growth medium.

13. The method of claim 12, wherein the method further comprises a step of converting the ester of 3-hydroxypropionic acid to 3-hydroxypropionic acid.

14. The method of claim 13, wherein the method further comprises a step of separating the 3-hydroxypropionic acid.

15. The method of claim 14, wherein the method further comprises the step of drying the 3-hydroxypropionic acid.

16. The method of claim 14, wherein the method further comprises a step of processing the 3-hydroxypropionic acid into other chemicals such as 3-hydroxypropionate salts (including ammonium, sodium and calcium 3-hydroxypropionate), 3-hydroxypropionate esters (including methyl, propyl and butyl esters), acrylic acid, acrylates, polyacrylic acid, acrylate polymers, acrylonitrile, acrylamide, acrolein, 1,3 propanediol and Reuterin.

17. The method of claim 1, wherein the method is for producing 3-hydroxypropionic acid, the method comprising:

culturing *Acetobacter lovaniensis* strain FJ1 having accession number NCIMB 41808 in a growth medium containing phosphate at a level which is between 10 and 30 g/liter, wherein culturing of the bacterium produces ethyl 3-hydroxypropionate;

separating the ethyl 3-hydroxypropionate from the growth medium;

converting the ethyl 3-hydroxypropionate to 3-hydroxypropionic acid;

separating the 3-hydroxypropionic acid; and optionally drying the 3-hydroxypropionic acid.

18. A method for producing an ester of 3-hydroxypropionic acid, the method comprising:

providing an aqueous medium containing a cell-free extract of an *Acetobacter lovaniensis* bacterium cultured in a growth medium containing phosphate at a level which is more than 2g/liter and up to 30 g/liter, wherein the ester of 3-hydroxypropionic acid is produced in the aqueous medium; and optionally separating the ester of 3-hydroxypropionic acid from the aqueous medium.

19. An aqueous medium containing a cell-free extract of an *Acetobacter lovaniensis* bacterium cultured in a growth medium containing phosphate at a level which is more than 2 g/liter and up to 30 g/liter, wherein the cell-free extract produces an ester of 3-hydroxypropionic acid, and wherein the ester of 3-hydroxypropionic acid is ethyl 3-hydroxypropionate.

* * * * *